United States Patent [19]

Nayfa

[11] Patent Number: 5,017,612
[45] Date of Patent: May 21, 1991

[54] PRESERVATIVE COMPOSITION AND METHOD

[76] Inventor: James E. Nayfa, 10310 Woodford, Dallas, Tex. 75229

[21] Appl. No.: 60,705

[22] Filed: Mar. 23, 1987

Related U.S. Application Data

[63] Continuation of Ser. No. 766,110, Aug. 15, 1985, abandoned.

[51] Int. Cl.$^5$ ...................... A01N 37/00; A61K 31/19
[52] U.S. Cl. ...................... 514/557; 424/78; 426/331; 514/642; 514/643
[58] Field of Search ...................... 514/557, 642, 643; 426/331; 424/78

[56] References Cited

U.S. PATENT DOCUMENTS

| | | | |
|---|---|---|---|
| 2,595,665 | 7/1971 | Huitson et al. | 514/557 |
| 3,595,665 | 7/1971 | Huitson et al. | 514/557 |
| 3,962,475 | 6/1976 | Forest et al. | 426/331 |
| 4,155,742 | 5/1979 | Sakurai et al. | 71/67 |
| 4,513,019 | 4/1985 | Brancq et al. | 424/494 |
| 4,518,547 | 5/1985 | Cuff et al. | 424/497 |

FOREIGN PATENT DOCUMENTS

| | | | |
|---|---|---|---|
| 592609 | 2/1960 | Canada | 514/557 |
| 144343 | 2/1962 | U.S.S.R. | 426/331 |

OTHER PUBLICATIONS

The Merck Index; 10th Edition, p. 150.

Primary Examiner—Stanley J. Friedman
Assistant Examiner—Kimberly R. Jordan
Attorney, Agent, or Firm—Sigalos, Levine & Montgomery

[57] ABSTRACT

A composition capable of preserving moisture-containing agriculture products succeptible to mold spoilage from mold spoilage for an extended period of time comprising a mold-inhibiting agent, a quaternary ammonium compound, and a polyglycol and the method of preserving agricultural products utilizing the composition.

10 Claims, No Drawings 5,017,612

PRESERVATIVE COMPOSITION AND METHOD

This application is a continuation, of application Ser. No. 766,110, filed Aug. 15, 1985 now abandoned on 3/23/87.

BACKGROUND OF THE INVENTION

It is well known that moisture-containing products, and in particular agricultural products such as grains and seeds tend to spoil in storage, particularly from fungal and particularly mold infestation.

A number of compounds and compositions have been utilized to prevent mold growth and protect moisture-containing products from spoilage and deterioration. Among the materials used are the acids such as sorbic acid, propionic acids, acetic acid and the salts thereof such as the calcium, sodium, and potassium salts. While generally satisfactory, it is known that mold-free storage time of various products treated with many of the above materials is a question of only a few weeks. Of the products tested, the most effective has been found to be propionic acid which when applied to a variety of materials such as grains, seeds, and the like can preserve them against mold spoilage for periods up to twelve months.

It is has been found, however, that all of these materials and in particular the acids, to have commercially acceptable mold-free storage time, must be utilized in amounts which make it very costly to apply Moreover, the acidic materials, such as propionic acid, when used in such amounts are extremely corrosive to the storage containers in which these seeds, grains, and the like are stored. As a consequence, the materials cause extensive damage to grain-storage and feed-storage facilities since they tend to corrode the metallic or deteriorate the concrete bins and silos in which grains and seeds are stored.

Also, some of the anti-fungal agents noted; such as propionic acid, have a strong odor and thus when used in the concentrations heretofore necessary have imparted that odor to the treated grains and seeds.

Attempts to utilize a lower concentration of the fungicides in relationship to the moisture content of the seeds and grains have been unsatisfactory since such lower concentrations have not acted to prevent fungal growth for the storage period desired.

SUMMARY OF THE INVENTION

Novel preservative compositions have been found that utilize a lower concentration of mold-inhibiting agents and yet still obtain the preserving time required without any substantial corrosive action on the storage vessels.

Briefly, the present invention comprises a composition capable of preserving a moisture-containing product succeptible to mold spoilage from spoilage for an extended period of time comprising a mold-inhibiting agent, a quaternary ammonium compound, and a polyglycol The invention also comprises the method of preserving such products as hereinafter described.

DETAILED DESCRIPTION

The present invention can be utilized with a wide variety of products that are succeptible of fungal; i.e., mold, infestation and is particularly effective with agricultural products, such as grains and seeds, to preserve the same. Among the products that can be preserved are grains and seeds such as corn, soybeans, rice, milo, sorghum, oats, wheat, barley, peanuts, cottonseed, and rapeseed. While the invention can be utilized with any of the above, it will be discussed specifically with respect to preservation of corn; it being understood it is equally applicable to all agricultural products to which anti-fungal agents, and particularly mold-inhibiting acids, can be added.

It is essential that the composition contain a mold-inhibiting agent, a quarternary ammonium compound, and a polyglycol.

As to the mold-inhibing agent, while sorbic acid and acetic acid can be used it is preferred to use propionic acid. Propionic acid is the most effective mold-inhibiting agent. Salts of propionic acid which hydrolyze in a fluid to release propionic acid can also be used as can the salts of sorbic and acetic acid and mixtures thereof.

The second essential component is the quaternary ammonium compound; preferably one in which the quaternary concentration is at least about 75% and particularly those made using tallow. Examples of suitable quaternary compounds are methyl-1-tallow amido ethyl-2-tallow imidazolinium-methyl sulfate, and dihydrogenated-tallow-methyl ammonium chloride. It is preferred to utilize those that are liquid at ambient temperature and for this reason the imidazolinium-methyl sulfate tallow compound identified above is preferred.

The third essential component is a polyglycol. While a variety of polyglycols can be used, it is preferred to use polyethylene glycol, although products being a combination of polyethylene and polypropylene glycol can also be utilized.

As to proportions, it is preferred that for each 100 parts by weight of mold-inhibiting agent in the composition that the quaternary compound be used in an amount from about 4 to 5 parts by weight and the polyglycol in an amount of from about 2 to 3 parts by weight.

The composition is preferably used in a fluid form and for that reason water or an alcohol such as isopropyl alcohol, where permitted, is added to make it easier as hereinafter set forth to apply the composition to the product to be protected. It has been found that a concentration of about 20% by weight of mold-inhibiting agent; such as propionic acid, in such fluid composition, is most suitable for commercial use with the quaternary compound and polyglycol being used in the corresponding concentrations set forth above.

While not completely understood, it is believed that the addition of the quaternary ammonium compound and the polyethylene glycol acts to ameliorate the effect of the propionic acid on the metal and concrete surfaces. But more importantly, they appear to act to make the propionic acid more readily adhere or apply to the individual kernels of corn, thus making it possible to place a lower concentration of propionic acid on the corn per any given moisture content of the corn and still maintain anti-fungal activity for long periods of time.

Extensive testing of concentration of propionic acid and other mold inhibitors on grains has been conducted by the U.S. Department of Agriculture Grain Marketing Research Center, Manhattan, Kansas, under the direction of Dr. David Sauer. Set forth below is a partial synopsis in the form of a table of Dr. Sauer's work as presented in 1973 to the American Society of Agricultural Engineers in Paper No. 73-707 entitled "Efficacy of Various Chemicals as Grain Mold Inhibitors" in which different lots of corn were adjusted to different moisture levels and to which the various mold inhibitors were added. The table shows mold-free storage time (in weeks) at various moisture contents (MC) of the corn and at two levels of addition of chemical.

TABLE I

| CHEMICAL APPLIED | 0.5% Application rate | | | 1.0% Application rate | | |
|---|---|---|---|---|---|---|
| | 18% MC | 20% MC | 22% MC | 18% MC | 20% MC | 22% MC |
| None | less than one week | | | less than one week | | |
| Potassium sorbate | 2 | 1 | 1 | 3 | 2 | 1 |
| Sorbic acid | 7 | 2 | 1 | 12 | 5 | 1 |
| Calcium propionate | 1 | 4 | 0 | 1 | 10 | 10 |
| Sodium propionate | 17+ | 5 | 3 | 17+ | 17+ | 17+ |
| Acetic Acid (glacial) | 17+ | 17+ | 7 | 17+ | 17+ | 12 |
| Propionic acid | 17+ | 17+ | 17+ | 17+ | 17+ | 17+ |

It will be noted that indeed propionic acid is the most effective preservative material and at concentrations of 0.5% and 1.0% application rate at least seventeen weeks of mold-free storage time on corn was obtained. The pounds of propionic acid required per ton of corn; utilizing the 0.5% and 1% application rate set forth in the table, range from about 10 to 20 pounds.

With the instant composition at the equivalent moisture content of corn set forth in the table of 18, 20, and 22 percent, mold-free times of seventeen weeks and longer are obtained utilizing only about 0.02 to 0.03% by weight of propionic acid per ton of corn; less than one-tenth the amounts previously used.

Again, while not completely understood, it is theorized that it is the ability of the quaternary compound and polyglycol to coat individual grains with the propionic acid and to maintain the acid in contact with the grains that enables the lesser amount of propionic acid to be effective. Thus, not only is a lower amount effective; which is an immense cost savings, but there is less corrosion of the storage metal and concrete surfaces and other handling equipment utilized for storing the grain and removing it from storage.

The application of the composition is largely evident from the description given.

As previously noted, the composition is preferably used in solution form in an inert fluid carrier such as water or an alcohol such as isopropyl alcohol where permitted and simply sprayed onto the grain as the grain is being placed into the storage container or other location. When so diluted, it is preferred that the fluid composition contain at least about 20% by weight of the mold-inhibiting agent and the corresponding amounts of quaternary compound and polyglycol. If desired, the mixture of propionic acid, quaternary compound, and polyglycol can be applied directly to the grain without the need of any carrier.

The amount applied is dependent upon the moisture content of the grain or seed to be preserved with larger amounts of the composition required for the higher moisture content products and the particular mold inhibitor used. Ordinarily, when propionic acid is used, from about 0.02 to 0.05 parts by weight of composition can be used for good preservation for each ton of product having moisture contents ranging from 10 to 36%. The optimum concentrations for other mold-inhibitors can be routinely determined by testing various concentrations on test batches of a grain or seed at various moisture contents.

The invention will be further described in connection with the following specific examples which are set forth for purposes of illustration only.

EXAMPLE 1

A composition was prepared by admixing the following components:

| | % by Weight |
|---|---|
| Propionic Acid | 20.01 |
| Methyl-1-tallow amido ethyl-2-tallow imidazolinium-methyl sulfate (VARISOFT 475 - Ashland Chem. Co.) | 0.87 |
| Polyethylene glycol (POLYGLYCOL 15-200 - Ashland Chem. Co.) | 0.55 |
| Water | 78.57 |

This composition was used to preserve large kernel yellow corn having a moisture content of 30% spraying the composition thereon by the use of low pressure nozzles in a standard applicator as the corn passed through the applicator.

The composition was applied to the corn at the rate of 3 lbs. per ton of corn and the corn then stored in a conventional concrete and metal storage bin.

After 10 months of storage periodic inspection showed no metal corrosion or concrete deterioration and the corn was mold-free and remained of the same grade and the odor of the propionic acid had dissipated.

For corn at various levels of moisture content, the amounts of this composition that can be added are set forth in the table that follows.

TABLE II

| Moisture Content (%) | 10-16 | 18 | 20 | 22 | 24 | 26 | 28 | 30 | 32 | 34 | 36 |
|---|---|---|---|---|---|---|---|---|---|---|---|
| Pounds of Aqueous Composition | 2 | 2 | 2½ | 3 | 3 | 3 | 3 | 3 | 4 | 4 | 5 |

EXAMPLE 2

The composition of Example 1 was applied to Funk variety cottonseeds having a moisture content of 14% at the rate of 2 lbs. per ton of cottonseeds and the thus treated cottonseeds stored in a corrugated metal silo.

After approximately 4½ months the cottonseeds were mold-free and their free fatty acid level was unaffected. Also there was no corrosion of the metal silo.

EXAMPLE 3

The composition of Example 1 was applied to Paymaster soybeans having a moisture content of 18% at the rate of 2 lbs. per ton of soybeans and the treated beans were stored in a concrete silo.

After approximately 4½ months the soybeans were still mold-free and remained at the same grade as when originally stored. There was also no deterioration of the concrete in the silo in contact with the soybeans.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A composition capable of preserving moisture-containing agricultural products succeptible to mold spoilage from mold spoilage for an extended period of time comprising a mold-inhibiting agent selected from acetic acid, sorbic acid, propionic acid and their hydrolyzable salts, or mixtures thereof, a quaternary ammonium compound and a polyglycol; said composition containing for each 100 parts by weight of said mold-inhibiting agent an amount of each of said quaternary compound and said polyglycol sufficient to permit said mold-inhibiting agent to preserve said moisture-containing agricultural products at a concentration of said mold-inhibiting agent lower than required when said mold-inhibiting agent is used without said quaternary compound and said polyglycol.

2. The composition of claim 1 wherein the mold inhibiting agent is propionic acid.

3. The composition of claim 2 wherein for each 100 parts by weight of propionic acid there is present from about 4 to 5 parts by weight of the quaternary ammonium compound and from about 2 to 3 parts by weight of the polyglycol.

4. The composition of claim 3 wherein said composition is a fluid composition containing at least about 20 parts by weight of propionic acid.

5. A method of preserving a moisture-containing agricultural product susceptible to mold spoilage from mold spoilage for an extended period of time comprising applying substantially uniformly to said product a composition comprising a mold-inhibiting agent selected from acetic acid, sorbic acid, propionic acid and their hydrolyzable salts, or mixtures thereof, a quaternary ammonium compound, and a polyglycol; said composition containing for each 100 parts by weight of said mold-inhibiting agent an amount of each of said quaternary compound and said polyglycol sufficient to permit said mold-inhibiting agent to preserve said moisture-containing agricultural product at a concentration of said mold-inhibiting agent lower than required when said mold-inhibiting agent is used without said quaternary compound and said polyglycol, the amount of said composition applied being sufficient to inhibit mold growth.

6. The method of claim 5 wherein the product is selected from corn, soybeans, rice, milo, sorghum, oats, wheat, barley, peanuts, cottonseed, or rapeseed and the mold-inhibiting agent is propionic acid.

7. The method of claim 6 wherein the composition contains for each 100 parts by weight of propionic acid, from about 4 to 5 parts by weight of the quaternary ammonium compound, and from about 2 to 3 parts by weight of the polyglycol.

8. The method of claim 7 wherein said composition is applied at the rate of about 0.02 to 0.05 percent by weight of propionic acid per ton of product.

9. A composition capable of preserving moisture-containing agricultural products succeptible to mold spoilage from mold spoilage for an extended period of time consisting essentially of propionic acid; a quaternary ammonium compound selected from methyl-1-tallow amido ethyl-2-tallow imidazolinium methyl sulfate or dihydrogenated tallow methyl ammonium chloride; and a polyglycol selected from polyethylene glycol or a mixture of polyethylene glycol and polypropylene glycol; said composition containing, for each 100 parts by weight of said propionic acid, from about 4 to 5 parts by weight of said quaternary ammonium compound and from about 2 to 3 parts by weight of said polyglycol.

10. A method of preserving a moisture-containing agricultural product susceptible to mold spoilage from mold spoilage for an extended period of time comprising applying substantially uniformly to said product in an amount sufficient to inhibit mold growth a composition consisting essentially of propionic acid; a quaternary ammonium compound selected from methyl-1-tallow amido ethyl-2-tallow imidazolinium methyl sulfate or dihydrogenated tallow methyl ammonium chloride; and a polyglycol selected from polyethylene glycol or a mixture of polyethylene glycol and a polypropylene glycol; said composition containing, for each 100 parts by weight of said propionic acid, from about 4 to 5 parts by weight of said quaternary ammonium compound and from about 2 to 3 parts by weight of said polyglycol.

* * * * *